(12) United States Patent
Helmlinger et al.

(10) Patent No.: US 6,326,349 B1
(45) Date of Patent: Dec. 4, 2001

(54) METHYLCYCLOTETRADEC-5-EN-1-ONES

(75) Inventors: Daniel Helmlinger, Dübendorf; Georg Fráter, Winterthur; Urs Müller, Dübendorf, all of (CH)

(73) Assignee: Givaudan Roure (International) SA, Geneva (CH)

( * ) Notice: Subject to any disclaimer, the term of this patent is extended or adjusted under 35 U.S.C. 154(b) by 0 days.

(21) Appl. No.: 09/388,020

(22) Filed: Sep. 1, 1999

(30) Foreign Application Priority Data

Sep. 3, 1998 (CH) .................................................. 1804/98

(51) Int. Cl.[7] ...................................................... A61K 7/46
(52) U.S. Cl. ................... 512/26; 512/8; 512/25; 512/27; 568/375
(58) Field of Search ................... 512/8, 25, 26, 512/27; 568/375

(56) References Cited

U.S. PATENT DOCUMENTS

| 4,183,965 | 1/1980 | Mookherjee et al. . |
| 5,354,735 | 10/1994 | Demole et al. . |

FOREIGN PATENT DOCUMENTS

| 55-66534 | 5/1980 | (JP) . |

OTHER PUBLICATIONS

Patent Abstracts of Japan, English language abstract of JP 55–66534 (1980).
Derwent English language abstract No. XP–002117059 of SU 627118 A (1978).
Yoshii, et al., *Chem. & Pharm. Bull.*, 17(3): 629–631 (1969).
Karpf, et al., *Helvetica Chimica Acta.*, 58(8): 2409–2422 (1975).
Thies, et al., *J. Org. Chem.*, 52(17): 3798–3806 (1987).

*Primary Examiner*—Jill Warden
*Assistant Examiner*—Monique T. Cole
(74) *Attorney, Agent, or Firm*—Bryan Cave LLP

(57) ABSTRACT

Disclosed are compounds of formula I having a strong musk-like odor:

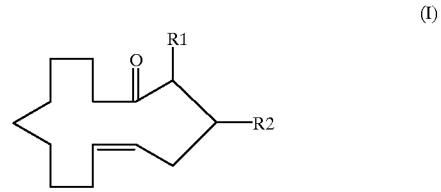

(I)

In formula I, $R^1$ and $R^2$ are hydrogen or methyl, with the proviso that when $R^1$ is methyl, $R^2$ is hydrogen, and when $R^1$ is hydrogen, $R^2$ is methyl. The compounds of formula I may be in the Z- and/or in the E-form. Methods of making the compounds of formula I and compositions containing such compounds are also disclosed.

16 Claims, No Drawings

METHYLCYCLOTETRADEC-5-EN-1-ONES

FIELD OF THE INVENTION

The invention relates to methylcyclotetradec-5-en-1-ones and to scent compositions which include at least one methylcyclotetradec-5-en-1-one.

BACKGROUND OF THE INVENTION

G. Ohloff, Fortschritte der chemischen Forschung (Advances in Chemical Research, Vol. 12/2, 201) reportedly states that macrocyclic carbonyl compounds having more than 13, but fewer than 19, carbon atoms are involved in achieving a musk odor. However, all commercial musk scents have ring sizes of 15, 16 or 17 carbon atoms. Extremely little is known about the olfactory properties of fourteen-membered ring ketones, and only then in isolated cases.

For example, Mookherjee, et al., U.S. Pat. No. 4,183,965 reportedly discloses the use of a mixture of 2- and 3-cyclotetradecen-1-one for reducing the bitter taste of foods. The compounds may also be used in perfumery and have a sweet, musk-like, exaltone-like, waxy, rooty odor.

JP-A 55-66534 reportedly discloses the synthesis of 5-cis-cyclotetradecen-1-one having a musk-like character by heating 1-vinyl-3-cis-cyclododecen-1-ol with an alkali metal or alkali metal hydride. E. Yoshi and S. Kimoto: Chem. Pharm. Bull 17, 629, 1969 and, subsequently, M. Karpf and A. S. Dreiding: Helvetica Chimica Acta, Vol. 58(8), 2409, 1975, reportedly disclose the synthesis of a mixture of cis- and trans-3-methylcyclotetradec-2-en-1-ones and 3-methylcyclotetradec-3-en-1-ones. Olfactory properties of these compounds are not given.

R. W. Thies and K. P. Daruwala: J. Org. Chem. 1987, 52, 3798 reportedly disclose the preparation of 3-methyl-trans-cyclopentadec-5-enone by treatment of trans- or cis-1-(1-propenyl)-trans-cyclotridec-3-en-1-ol with potassium hydride in hexamethylphosphoramide.

Demole, et al., U.S. Pat. No. 5,354,735 reportedly discloses cis- and transisomers of 3-methylcyclopentadec-5-en-1-one as scent constituents having musk-like properties. The cis-isomer is stronger, more elegant, and has more of a musk odor and less of an animal odor than the trans-isomer, which has more of a nitromusk character and ambrette seed odor.

SUMMARY OF THE INVENTION

Accordingly, the present invention provides compounds of formula I:

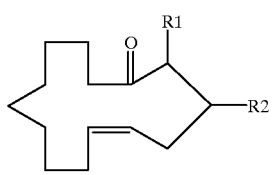

(I)

wherein $R^1$ and $R^2$ are hydrogen or methyl, with the proviso that, when $R^1$ is methyl, $R^2$ is hydrogen, and when $R^1$ is hydrogen, $R^2$ is methyl.

The invention also provides scent compositions having at least one compound of formula I.

In addition, the present invention also provides processes for preparing organoleptic compositions. This process includes combining a compound according to formula I defined herein with a perfume or a consumer product.

DETAILED DESCRIPTION OF THE INVENTION

The present invention provides compounds of formula I:

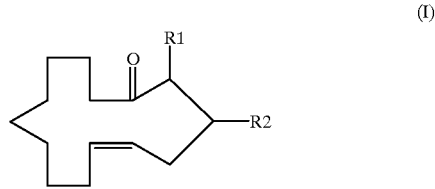

(I)

wherein $R^1$ and $R^2$ are hydrogen or methyl, with the proviso that, when $R^1$ is methyl, $R^2$ is hydrogen, and when $R^1$ is hydrogen, $R^2$ is methyl. Unexpectedly, these compounds have a strong musk-like, i.e. nitromusk-like, powdery, fruity odor. These compounds also have a low threshold value and very good substantivity. The compounds of formula I may be in the Z- and/or in the E-form.

A preferred compound of formula I is E-3-methylcyclotetradec-5-en-1-one. Surprisingly, this compound has an odor which is more than ten times stronger than the corresponding Z-compound, Z-3-methylcyclotetradec-5-en-1-one. E-3-methylcyclotetradec-5-en-1-one has a gas-chromatographic threshold value of 0.2 ng/l while Z-3-methylcyclotetradec-5-en-1-one has one of 2.2 ng/l.

The compounds of formula I may, like other known musk scents, be used generally, i.e., they may be used to harmonize with a large number of natural and synthetic products which are frequently used in scent compositions. Particularly in the base note, compounds of formula I achieve interesting effects in combination with amber-like and woody accords, such as patchouli oil, cedarwood scent, and sandalwood scent. Floral body (middle) notes impart elegance and radiance to the compounds of formula I. Examples of different classes of substances that harmonize particularly well with the compounds of formula I include:

Natural products, such as oakmoss absolute, geranium oil, jasmine absolute, patchouli oil, rose oil, sandalwood oil, vetiverol, ylang ylang oil, and the like;

Alcohols, such as citronellol, EBANOL®, geraniol, linalool, phenyl ethyl alcohol, SANDALORE®, and the like;

Aldehydes and ketones, such as FLOROZONE® (3-(4-ethylphenyl)-2,2-dimethylpropional), HYDROXY-CITRONELLAL ISO-E-SUPER®, ISORALDEIN®, maltol, methyl cedryl ketone, methylionone, vanillin, and the like;

Ethers and acetals, such as ambrox, geranyl methyl ether, rose oxide and SPIRAMBRENE® (2',2',3,7,7-pentamethyl-spiro[bicyclo[4.1.0]heptan-2-5'-[1,3]dioxanel], and the like; and Esters and lactones, such as BERRYFLOR®, γ-decalactone, γ-undecalactone, and the like.

The compounds of formula I may be used to prepare various compositions using a broad range of known scents and scent mixtures as indicated in the list set forth above.

The advantageous properties of the compounds of formula I permit broad and diverse use. For example, the compounds of formula I may be used in sweet oriental creations or in the fragrance trends "fougère," "chypre" and "floral."

Because of the low threshold values and good substantivity, the compounds of formula I may be used both in luxury perfumery, in compositions for cosmetic products, and for mass-produced products, such as detergents.

The compounds of formula I may be used within wide concentration limits, that may range, for example, from about 0.1% by weight in detergents to about 40% by weight in alcoholic solutions. Preferred concentrations of the compounds of formula I range between 3 and 20% by weight. Concentrations outside these limits, however, are also possible because the experienced perfumer may achieve novel effects using lower or higher concentrations.

In the present invention, compositions which include one or more of the compounds of formula I may be combined with all types of scent compositions including perfumes and perfumed consumer products, such as caux de cologne, eaux de toilette, extraits, lotions, creams, shampoos, soaps, ointments, powders, deodorants, detergents, other household products, and the like.

In the preparation of such compositions, the compounds of formula I may be used together with other scents or scent mixtures in a known manner, as described, for example, by W. A. Poucher, Perfumes, Cosmetics, Soaps, Vol. 2, 7th edition Chapman and Hall, London 1974.

The compounds of formula I may be prepared by various methods. For example, a compound of formula I in which $R^1$ is H and $R^2$ is $CH_3$ is prepared by the following method as a mixture with a compound of formula II:

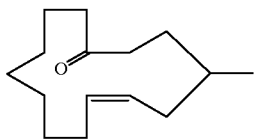

(II)

i.e., a mixture of cis- and trans-4-methylcyclotetradec-6-en-1-one. In this method, (4-carboxy-3-methylbutyl) triphenylphosphonium bromide is subjected to a Wittig reaction, for example by treatment with potassium t-butoxide in tetrahydrofuran and subsequent addition of methyl 9-oxononanoate. The resulting product, dimethyl 3-methyltetradec-5-enedioate is subjected to an acyloin condensation and then treated with acetic anhydride/pyridine. The resulting mixture of mainly Z-4-methyl-2-oxocyclotetradec-6-enyl acetate and Z-3-methyl-14-oxocyclotetradec-5-enyl acetate is treated with calcium in ammonia at a low temperature (e.g., between about $-30°$ C. to about $-70°$ C.). The excess calcium is destroyed using bromobenzene.

This method produces a mixture of the following compounds:

E-3-methyl-cyclotetradec-5-enone 11%

Z-3-methyl-cyclotetradec-5-enone 35%

Z-4-methyl-cyclotetradec-6-enone 49%

These compounds have strongly musk-like (nitromusk), powder-like odors.

In the present invention, another example of a method for preparing a compound of formula I ($R^1$=H, $R^2$=$CH_3$), preferably in the trans-form, begins with 2-chlorocyclododecanone or 2-bromocyclododecanone as starting materials. These compounds may be obtained in one stage from cyclododecanone (See, e.g., JP 491 093 39 and EP-A-051 233). Treatment of 2-chlorocyclododecanone with lithium carbonate in N-methylpyrrolidone at reflux temperature produces a mixture of the following compounds:

5% of Z-cyclododec-2-en-1-one

6% of E-cyclododec-2-en-1-one

13% of cyclododecanone

57% of E-cyclododec-3-en-1-one

16% of Z-cyclododec-3-en-1-one

This mixture is treated with propenylmagnesiumbromide in tetrahydrofuran. This produces a mixture of mainly cis/trans-1-(1-propenyl)cyclododec-3-en-1-ol. After treatment with sodium hydride in N-methylpyrrolidone, a mixture is formed of E-3-methylcyclotetradec-5-en-1-one, Z-3-methylcyclotetradec-5-en-1-one (E:Z=3:1), and the two diastereomers of 3-methyl-4-vinylcyclododecanone.

This mixture has an odor that is very strongly musk-like (nitromusk), powdery, linear, like fresh laundry (dried in the sun). The weak, woody odor of the two diastereomeric 3-methyl-4-vinylcyclododecanones is completely concealed by the two musk compounds E-3-methylcyclotetradec-5-en-1-one and Z-3-methyl-cyclotetradec-5-en-1-one according to the invention.

A similar mixture of E- and Z-3-methylcyclotetradec-5-en-1-one may be obtained by pyrolysis of the silyl ether of cis/trans propenylcyclododec-3-en-1-ol.

The compounds of formula I ($R^1$=$CH_3$, $R^2$=H) may be prepared as follows:

A mixture of mainly E-cyclododec-3-en-1-one (74%) and Z-cyclododec-3-en-1-one (19%) is treated with isopropenyl-magnesium bromide in tetrahydrofuran, to form mainly E-1-isopropenylcyclododec-3-en-1-ol. The purified E-1-isopropenylcyclododec-3-en-1-ol is treated with potassium hydride in N,N-dimethylacetamide in the presence of 18-crown-6, that forms a mixture of diastereomeric 2-methyl-4-vinylcyclododecanone and E-2-methylcyclotetradec-5-en-1-one.

The E-2-methylcyclotetradec-5-en-1-one has a musk (nitromusk), powdery, sweet odor.

The following, examples are provided to further illustrate certain of the compounds of the present invention, processes for making such compounds, as well as certain physical properties and uses thereof. These examples are illustrative only and are not intended to limit the scope of the invention in any way.

EXAMPLES

Example 1

143 g (0.313 mol) of (4-carboxy-3-methylbutyl) triphenylphosphonium bromide were pulverized and introduced into 630 ml of tetrahydrofuran. The resulting suspension was stirred for 10 minutes, cooled to $-20°$ C., and slurried rapidly with 70 g (0.625 mol) of potassium t-butoxide in 315 ml of tetrahydrofuran. The temperature increased to 0° C. and the reaction mixture turned orange. The mixture was then stirred for 45 minutes at between $-5°$ C. and 0° C.

The mixture was then cooled to $-20°$ C. and 76 g (purity 70%) (0.285 mol) of methyl 9-oxononanoate were added to the mixture. The temperature increased to $-1°$ C. The mixture was allowed to warm to room temperature (1.5 hours) and was stirred for another hour at 40° C.

The reaction mixture was poured onto 1.5l of iced water, adjusted to a pH of 14 using 25 ml of 30% NaOH, and extracted with 2×700 ml of ether. The pH of the aqueous phases was adjusted to 2–3 using 100 ml of ortho-phosphoric acid, and the phases were extracted with 2×500 ml of ether. The organic phase was washed with 300 ml of water and 300 ml of saturated sodium chloride solution, dried over $Na_2SO_4$, and concentrated by evaporation.

The crude product (102.9 g) was diluted with 360 ml of methanol, 3.4 g of p-toluenesulfonic acid were added thereto, and the mixture was refluxed for 3.5 hours. An excess of $NaHCO_3$ (solid) was added to the mixture which was then concentrated by evaporation. The crude product (108.9 g) was chromatographed over 1 kg of silica gel 60 (Merck) (0.040 mm–0.063 mm) with 61 of hexane/ether 4:1 and 21 of hexane/ether 3:1. 57.3 g of dimethyl Z-3-methyltetradec-5-enedioate were obtained.

Spectroscopic data for the product are set forth below:
IR (liquid): 3004; 2928; 2855; 1740; 1458; 1436; 1364; 1251; 1198; 1168; 1011.
NMR: ($CDCl_3$, 200 MHz) 5.4 (2H) m; 3.66 (6 H) s.
MS: 298 (0.8); 266 (20); 248 (7); 235 (34); 224 (60); 206 (10); 192 (28); 175 (8); 164 (19); 150 (25); 136 (19); 123 (18); 109 (38); 95 (66); 87 (30); 81 (94); 75 (69); 68 (69); 59 (75); 55 (100); 41 (88); 29 (27).

Example 2

A dry apparatus with an oil bath was charged with 21 of xylene, and argon gas was passed through the apparatus for 30 minutes. The oil bath was heated to 148° C. At an internal temperature of 100° C., 17.2 g (0.750 mol) of sodium were added in portions to the xylene. A solution of 56 g (0.188 mol) of dimethyl Z-3-methyltetradec-5-enedioate in 150 ml of xylene was then added dropwise to the mixture over the course of 4 hours. The internal temperature increased to 134° C.

The mixture was then stirred for 30 minutes at this temperature and then cooled to room temperature. 120 ml of EtOH and 50 ml of water were added dropwise to the mixture. The organic phase was washed with 400 ml of water and 200 ml of saturated sodium chloride solution, dried over $Na_2SO_4$, and concentrated by evaporation.

In this way, 36.6 g of crude product were obtained. This crude product was dissolved in 75 ml of pyridine, 15.4 g of acetic anhydride were added, and the mixture was stirred for 4 hours at 80° C. The product was poured onto 400 ml of iced water, adjusted to pH 2 using concentrated hydrochloric acid and extracted with 2×200 ml of ether. The organic phases were washed with water and saturated sodium chloride solution, dried over sodium sulfate, and concentrated by evaporation.

This method produced 41.5 g of a crude product, which was chromatographed over 1 kg of silica gel 60 (Merck) (0.040 mm–0.063 mm). 30.9 g of a mixture of mainly Z-4-methyl-2-oxocyclotetradec-6-enyl acetate and Z-3-methyl-14-oxocyclotetradec-5-enyl acetate were obtained.

Spectroscopic data for this mixture are set forth below:
IR (liquid): 3006; 2928; 2857; 1746; 1727; 1461; 1373; 1236; 1087; 1026.
NMR: ($CDCl_3$, 200 MHz) 5.45 (2H) m; 5.1 (2H) m; 2.15 (3H) s.
MS: 280 (1); 238 (9); 220 (9); 202 (3); 191 (1); 177 (4); 163 (4); 149 (5); 135 (7); 121 (12); 111 (16); 95 (20); 81 (28); 67 (18); 55 (28); 43 (100); 29 (8).

Example 3

1.41 of ammonia were added to 35.8 g (0.893 mol) of calcium at −50° C. over the course of 20 minutes. The mixture was then stirred at −60° C. for 20 minutes. 30 g of a mixture of mainly Z-4-methyl-2-oxocyclotetradec-6-enyl acetate and 7-3-methyl-14-oxocyclotetradec-5-enyl acetate in 330 ml of tetrahydrofuran were added dropwise at −50° C. over the course of 2 hours, and the mixture was stirred at −70° C. for 15 minutes. 160 ml of bromobenzene were then added dropwise over the course of 30 minutes. The mixture was allowed to warm to room temperature, and the ammonia was removed by evaporation. The product was then poured onto ice, acidified to pH 3 using ortho-phosphoric acid, and extracted with ether. The organic phase was washed with water and saturated sodium chloride solution, dried over $Na_2SO_4$, and concentrated by evaporation. The crude product (39.8 g) was chromatographed over 800 g of silica gel 60 (Merck) (0.040–0.063 mm). This method produced 13.7 g of a mixture of the following compounds:

E-3-methyl-cyclotetradec-5-enone 11%
Z-3-methyl-cyclotetradec-5-enone 35%
Z-4-methyl-cyclotetradec-6-enone 49%

The odor of the mixture was musk (nitromusk), powdery.
The odor of the E-3-methylcyclotetradec-5-enone was musk, powdery, animal, ambergris-like.

The individual compounds were obtained in pure form by additional chromatography over silica gel (0.040–0.063 mm) using 10% silver nitrate.

Spectroscopic data of each compound is set forth below:

Z-3-methylcyclotetradec-5-enone

IR: (liquid): 3008; 2929; 2859; 1710; 1460; 1408; 1369; 1047; 718.
$^1$H-NMR: ($CDCl_3$ 200 MHz) 5.46 (2H) m; 1.0 (3H) d; J=7.5 Hz.
$^{13}$C-NMR: ($CDCl_3$) 211.2 (s); 131.6 (d); 126.7 (d); 49.6 (t); 40.2 (t); 32.8 (t); 30.6 (d); 27.3(t); 26.1 (t); 25.6 (t); 25.0 (t); 24.7 (t); 21.1 (t); 20.1 (q).
MS: 222 (25); 207 (5); 193 (4); 179 (11); 164 (17); 147 (8); 135 (17); 121 (19); 109 (33); 95 (58); 81 (100); 68 (94); 55 (89); 41 (94); 29 (25).

Z-4-methylcyclotetradec-6-enone

IR (liquid): 3007; 2928; 2858; 1711; 1461; 1408; 1375; 1287; 1124; 1046; 712.
$^1$H-NMR: ($CDCl_3$, 200 MHz) 5.35 (1H) m; 5.48 (1H) m; 0.96 (2H) d; J=7.5 Hz.
$^{13}$C-NMR: ($CDCl_3$) 212.1 (s); 130.8 (d); 127.7 (d); 40.2 (t); 39.7 (t); 33.4 (d); 33.4 (t); 30.8 (t); 27.0 (t); 26.7 (t); 26.1 (t); 25.5 (t); 25.2 (t); 23.2 (t); 19.6 (q).
MS: 222 (33); 204 (4); 193 (3); 179 (15); 165 (14); 147 (10); 135 (12); 125 (21); 111 (47); 98 (56); 81 (60); 67 (55); 55 (100); 41 (70); 29 (23).

E-3-methylcyclotetradec-5-enone

IR (liquid): 2928; 2856; 1708; 1458; 1441; 1365; 970
H-NMR: ($CDCl_3$ 400 MHz) 5.32 (2H) m; 2.86 (1H) dd, J=17 Hz, J=2 Hz; 2.33 (1H) m; 0.95 (3H) d; J=6.6 Hz.
$^{13}$C-NMR: ($CDCl_3$) 212.4 (s); 132.8 (d); 129.9 (d); 46.2 (t); 42.9 (t); 31.1 (t); 29.0 (d); 27.2 (t); 26.5 (t); 25.2 (t); 24.8 (t); 24.5 (t); 23.3 (t); 21.1 (q).
MS: 222 (69); 207 (14); 193 (6); 179 (15); 164 (34); 154 (1); 147 (12); 135 (30); 123 (26); 109 (41); 95 (69); 81 (100); 67 (76); 55 (63); 41 (57); 28 (16).

Example 4

100 g of lithium carbonate (1.35 mol, pulverized) and 260 g (1.2 mol) of 2-chlorocyclododecanone were added to 1.21 of N-methylpyrrolidone. The mixture was heated to 180°–185° C. with stirring, and $CO_2$ was eliminated (time:

3 hours). The crude mixture was cooled, poured onto 2.5 l of water, and extracted by shaking three times with hexane. The organic phase was washed three times with water, dried, and concentrated by evaporation. The crude product (238 g) was distilled under a high vacuum (0.1 mm). After an initial fraction (4.9 g), 105 g of a product having a boiling point of from 89 to 95° C./0.1 mm was obtained. The gas chromatographic analysis revealed the presence of the following compounds in the product:

5% of Z-cyclododec-2-en-1-one

6% of E-cyclododec-2-en-1-one

13% of cyclododecanone

57% of E-cyclododec-3-en-1-one

16% of Z-cyclododec-3-en-1-one

Spectroscopic data of two of these compounds is set forth below:

Z-cyclododec-3-en-1-one $^{13}$C-NMR: (CDCl$_3$) 211.0 (s); 132.0 (d); 122.9 (d); 43.4 (t); 37.7 (t); 26.6 (t); 26.3 (t); 24.3 (t); 24.1 (t); 23.5 (t); 23.0 (t); 22.6 (t).

MS: 180 (62); 162 (6); 151 (19); 137 (25); 123 (25); 111 (52); 98 (100); 81 (68); 67 (82); 54 (84); 41 (60); 27 (12).

E-cyclododec-3-en-1-one

H-NMR: (CDCl$_3$ 400 MHz) 5.7–5.61 d,t,t (1H); J=15.3 Hz; J=1.2 Hz; J=7.4 Hz; 5.34–5.43 d,t,t (1H); J=15.2 Hz; J=1.2 Hz; J=7.6 Hz; 3.04 (2H) d; J=7.6 Hz; 2.48 (2H) t; J=6.8 Hz; 2.03 (2H) m.

$^{13}$C-NMR: (CDCl$_3$) 209.7 (s); 136.3 (d); 122.8 (d); 48.3 (t); 39.6 (t); 32.2 (t); 26.3 (t); 25.4 (t); 24.9 (t); 24.1 (t); 23.9 (t); 22.1 (t).

MS: 180 (68); 162 (62); 151 (17); 137 (23); 123 (23); 111 (51); 98 (100); 81 (63); 67 (80); 54 (86); 41 (61); 27 (12).

Example 5

8.26 g of magnesium (0.34 mol) were activated with a few crystals of iodine, 25 ml of tetrahydrofuran were added, and 41 g (0.34 mol) of 1-bromo-1-propene (cis/trans mixture) dissolved in 120 ml of tetrahydrofuran was slowly added dropwise at 70° C. (dropping time 1.5 hours). The mixture was stirred at this temperature for 3 hours.

The mixture was then cooled to 0° C., and 51.2 g of a mixture of mainly E-cyclododec-3-en-1-one (62%), Z-cyclohex-3-en-1-one (18%), and E-cyclododec-2-en-1-one (7%), prepared as in Example 4, and dissolved in 100 ml of tetrahydrofuran, were added dropwise over the course of 30 minutes. The mixture was stirred at room temperature for 1.5 hours, then saturated ammonium chloride solution cooled in ice and water was added, followed by addition of 100 ml of ether and 37 g of phosphoric acid.

The phases were separated and extracted twice with ether. The organic phase was washed with saturated sodium chloride solution, dried, and concentrated by evaporation. 60.7 g (96%) of a crude product were obtained, containing a mixture of mainly 1-cis/1-trans-propenylcyclododec-3-en-1-ol. To characterize the compounds formed, 3.6 g of the crude product were chromatographed over 110 g of silica gel 60 (Merck) (0.04–0.063 mm) (elution: hexane/ether, firstly 9:1, then 2:1).

Spectroscopic data of (1E,3 E)-1-(1-propenyl) cyclododec-3-en-1 -ol is set forth below:

H-NMR: (CDCl$_3$ 400 MHz) 5.71–5.51 (31H) m; 5.51–5.4 (1H) m; ABX System: 2.33 (1H) dd, J=7.6; J=14 Hz, 2.25 (1H) dd J=6 Hz, J=14 Hz; 2.1 (2H) dd; J=5.6; J=5.6; 1.7 (3H) d, J=5 Hz.

$^{13}$C-NMR: (CDCl$_3$) 138.1 (d); 134.7 (d); 125.3 (d); 122.8 (d); 74.7 (s); 43.0 (t); 37.1 (t); 33.3 (t); 28.6 (t); 27.0 (t); 26.0 (t); 25.5 (t); 24.3 (t); 19.0 (t); 17.8 (q).

MS: 222 (2); 207 (17); 204 (64); 189 (7); 179 (9); 175 (10); 161 (12); 147 (16); 133 (26); 119 (33); 105 (51); 97 (60); 91 (58); 84 (69); 79 (55); 69 (100); 55 (29); 41 (35); 29 (6).

Spectroscopic data of (1-Z,3E)-1-(1-propenyl) cyclododec-3-en-1-ol is set forth below:

H-NMR: (CDCl$_3$, 400 MHz) 5.69–5.3 (4H) m; 2.4 (2H) d; J=6.5 Hz, 2.11 (211) dd; J=6 Hz; J=6 Hz; 1.9 (3H) d; J=5.5 Hz.

$^{13}$C-NMR: (CDCl$_3$) 136.2 (d); 134.9 (d); 126.5 (d); 125.3 (d); 75.8 (s); 44.6 (t); 37.8 (t); 33.3 (t); 28.5 (t); 27.1 (t); 26.0 (t); 25.1 (t); 24.3 (t); 19.1 (t); 14.5 (q).

MS: 222 (1); 208 (14); 204 (27); 189(3); 179 (7); 175 (6); 166 (5); 161 (6); 151 (9); 147 (8); 133 (12); 124 (12); 119 (16); 105 (25); 97 (44); 91 (28); 84 (51); 79 (29); 69 (100); 55 (20); 41 (25); 29 (4).

Example 6

A dried apparatus was charged with 11.1 g of propenylcyclododec-3-en-1-ol prepared as in Example 5 (crude product) in 150 ml of N-methylpyrrolidone, and 4.8 g of sodium hydride (55%) were added. Hydrogen started to evolve at a moderate rate, and the temperature increased to 30° C. The mixture was then stirred for 5 hours at 85° C., allowed to cool, and 20 ml of water were then added dropwise to the mixture.

The product was poured onto 200 ml of iced water, adjusted to pH 5 with 10 ml of phosphoric acid, and extracted with ether. The organic phase was washed with water and saturated sodium chloride solution, dried, and concentrated by evaporation. The product (13.6 g) was chromatographed (380 g of silica gel, 0.04–0.063 mm: elution: hexane/ether 19:1 and 8:1). This process formed 3.6 g of product in addition to 2.7 g of starting material. The product was a mixture of mainly E-3-methylcyclotetradec-5-en-1-one, Z-3-methylcyclotetradec-5-en-1-one (EZ:=3:1) and erythro and threo 3-methyl-4-vinylcyclododecanone.

This mixture has an odor which is very strongly musk-like (nitromusk), powdery, linear, like fresh laundry (dried in the sun). The individual compounds were purified by additional chromatography over 10% NO$_3$Ag silica gel.

Spectroscopic data for 3-methyl-4-vinylcyclododecanone (1. diastereomer) is set forth below:

IR (liquid): 3074; 2932; 2866; 1707; 1637; 1467; 1445; 1368; 1323; 1173; 1037;994;911.

H-NMR: (CDCl$_3$, 200 MHz); 5.7 (1H) m; 5.08 (1H) m; 5.0 (1H) m; 2.96 (1H) dd; J=18 Hz; J=11 Hz; 0.84 (3H) d; J=7.5 Hz.

$^{13}$C-NMR: (CDCl$_3$) 211.6 (s); 141.3 (d); 114.8 (t); 44.4 (t); 43.4 (t); 41.1 (d); 31.8 (d); 5 26.0 (t); 24.4 (t); 23.5 (t); 23.0 (t); 22.7 (t); 22.5 (t); 14.9 (q).

MS: 222 (1); 207 (2); 193 (5); 165 (4); 151 (8); 37 (14); 123 (17); 109 (29); 95 (42); 81 (60); 67 (90); 55 (98); 41 (100); 29 (27).

Spectroscopic data for 3-methyl-4-vinylcyclododecanone (2. diastereomer) is set forth below:

H-NMR: (CDCl$_3$, 400 MHz); 5.55 (1H) m; 5.08 (1H) m; 5.05(1H) m; 0.9 (3H) d; J=7 Hz.

$^{13}$C-NMR: (CDCl$_3$) 211.7 (s); 138.6 (d); 116.4 (t); 49.6 (t); 43.10 (d); 38.2 (t); 32.1 (d); 30.7 (t); 26.0 (t); 23.87 (t); 23.85 (t); 23.5 (t); 22.8 (t); 21.7 (t); 16.0 (q).

MS: 222 (15); 207 (22); 193 (28); 180 (6); 179 (24); 175 (27); 165 (25); 151 (31); 137 (54); 123 (58); 109 (70); 95 (76); 81 (84); 67 (95); 55 (100); 41 (81); 29 (15).

Example 7

7 g (0.3 mol) of magnesium were coated with a layer of a small amount of tetrahydrofuran (50 ml). 3 g of 2-bromopropene in 28 ml of tetrahydrofuran was added. The mixture was warmed briefly, and the reaction started. 27 g of 2-bromopropene dissolved in 160 ml of tetrahydrofuran were then added dropwise over the course of 90 minutes. An ice bath was used for cooling, so that the temperature remained between 55° C. and 60° C.

The mixture was then refluxed for 20 minutes and cooled (20° C.). 40 g (0.222 mol) of a mixture of mainly E-cyclododec-3-en-1-one (74%) and Z-cyclododec-3-en-1-one (19%) dissolved in 50 ml of tetrahydrofuran were added dropwise over the course of 1 hour. The temperature was not allowed to exceed 35° C. The mixture was then stirred for 20 minutes at room temperature.

The reaction product was poured onto a mixture of ice/water and ammonium chloride, extracted with methyl t-butyl ether, washed with water and saturated sodium chloride solution, dried over magnesium sulfate, and concentrated by evaporation. The crude product (48 g) was chromatographed (hexane, methyl t-butyl ether 9:1). This method produced 37 g of E-1-isopropenylcyclododec-3-en-1-ol. Recrystallization produced a product (33 g) with a purity of 95%:

Spectroscopic data of E-1-isopropenylcyclododec-3-en-1-ol is set forth below:

IR (KBr): 3285; 2988; 2932; 2861; 1641; 1448; 1396; 1368; 1212; 1024; 1003; 981; 898; 700.

H-NMR: (CDCl$_3$, 400 MHz); 5.43–5.73 (2H) m; 4.8–5 (2H) m; 1.8 (3H) m.

$^{13}$C-NMR: (CDCl$_3$) 150.22 (s); 134.67 (d); 125.71 (d); 110.30 (t); 76.66 (s); 41.27 (t); 34.64 (t); 33.24 (t); 28.42 (t); 26.98 (t); 26.00 (t); 24.93 (t); 24.42 (t); 19.22 (t); 18.81 (q).

Example 8

200 ml of N,N-dimethylacetamide and 34 g of 18-crown-6 (Fluka) were added to 25 g (0.125 mol) of potassium hydride (20% in oil). 18 g (0.085 mol) of E-1-isopropenylcyclododec-3-en-1-ol (purity 95%) was then added and heated rapidly to 120° C. An orange-red solution was formed, which was maintained at 120° C. for 1 minute and then allowed to cool to room temperature.

The reaction mixture was poured onto water, ice, and citric acid and was then extracted with hexane. The organic phase was washed with water and saturated sodium chloride solution until neutral, dried over magnesium sulfate, and concentrated by evaporation. The crude product (20 g) was chromatographed with hexane and methyl t-butyl ether. This produced 4.2 g of a mixture of diastereomeric cyclododecanone, 6.2 g of a mixture of diastereomeric 2-methyl-4-vinylcyclododecanone, E-2-methylcyclotetradec-5-en-1-one, and 3 g of pure E-2-methylcyclotetradec-5-en-1-one.

Spectroscopic data of the mixture of diastereomeric 2-methyl-4-vinylcyclododecanone is set forth below:

IR (liquid): 3075; 2931; 2864; 1705; 1639;1465; 1444; 1360; 912.

H-NMR: (CDCl$_3$, 200 MHz) 5.25–5.65 (1H)m; 5.1–4.9 (2H)m; 1.11 (3H) d; J=6.5 Hz.

MS: 222 (14); 207 (7); 193 (24); 180 (8); 179 (17); 175 (19); 175 (22); 150 (75); 137 (27); 123 (53); 109 (77); 95 (83); 81 (100); 67 (90); 55 (99); 41 (80); 29 (15).

Spectroscopic data of E-2-methylcyclotetradec-5-en-1-one is set forth below:

IR (liquid): 2929; 2854; 1704; 1458; 1374; 972.

H-NMR: (CDCl$_3$, 200 MHz); 5.35 (2H)m; 1.05 (3H) d; J=6.5 Hz.

$^{13}$C-NMR: (CDCl$_3$) 215.75 (s); 132.05 (d); 130.34 (d); 41.08 (t); 40.58 (d); 31.41 (t); 30.81 (t); 29.38 (t); 26.88 (t); 26.33 (t); 25.93 (t); 24.63 (t); 24.61 (t); 22.92 (t); 15.14 (q).

MS: 222 (100); 207 (4); 193 (41); 175 (17); 165 (31); 150 (46); 140 (34); 135 (24); 121 (40); 109 (61); 95 (77); 81 (85); 67 (94); 55 (89); 41 (77); 99 (15).

Example 9

A fabric softener composition containing a compound of formula I was made as set forth below:

Fabric Softener Accord

|  | Proportion by weight |
|---|---|
| E-3-Methylcyclotetradec-5-en-1-one (Example 3) | 30 |
| Phenylethyl acetate | 30 |
| Benzyl alcohol extra | 100 |
| Hexylcinnamaldehyde | 150 |
| Citronellol extra | 50 |
| Coumarin | 20 |
| Dynascone 10 | 1 |
| Floralozon | 4 |
| Isoraldein 70 | 100 |
| Lilial | 250 |
| Linalool synt. | 100 |
| Methylacetophenone | 5 |
| Methyl cedryl ketone | 50 |
| Radjanol | 10 |
| Amyl salicylate | 50 |
| Terpineol | 50 |
|  | 1000 |

The compound prepared as in Example 3 provided volume and cleanliness to this floral, woody accord for a fabric softener. As a result of good substantivity, the compound freshness and cleanliness exhibited in the fabric softener were also retained in dried laundry treated with such a fabric softener.

Example 10

A perfume composition containing a compound prepared as in Example 3 is set forth below:

Fine Fragrance Accord

|  | Proportion by weight |
|---|---|
| E-3-Methylcyclotetradec-5-en-1-one (Example 3) | 50 |
| Benzyl acetate | 15 |
| Ethyl acetoacetate | 25 |
| Ethyl phenyl alcohol | 60 |
| Hexylcinnamaldehyde | 70 |
| Ambrettolide | 10 |
| Ambrofix | 2 |
| Ethylene brassylate | 100 |
| Citronellol extra | 50 |
| Cyclogalbonate | 4 |
| Cyclohexal | 20 |
| Ethyllinalool | 80 |
| Oxyoctalin formate | 15 |
| Gardenol | 2 |
| Givescon | 15 |
| Hedion | 300 |
| Indole 10% PE | 2 |
| Isoraldein 95 | 35 |

-continued

| | Proportion by weight |
|---|---|
| cis-Jasmone | 3 |
| Lilial | 80 |
| Methyl pamplemousse | 20 |
| Black pepper ess. | 10 |
| Tricyclal | 2 |
| Tropional | 30 |
| | 1000 |

The compound prepared as in Example 3 imparts an organoleptically pleasing odor, e.g., a musk-like powdery effect to the floral, transparent accord of the alcoholic perfume's richness, that combines harmoniously with the floral, fruity part of the accord.

The invention being thus described, it will be obvious that the same may be varied in many ways. Such variations are not to be regarded as a departure from the spirit and scope of the invention and all such modifications are intended to be included within the scope of the following claims.

We claim:

1. A compound according to formula I:

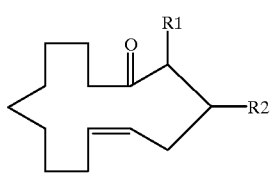

(I)

wherein $R^1$ and $R^2$ are hydrogen or methyl with the proviso that, when $R^1$ is methyl, $R^2$ is hydrogen, and when $R^1$ is hydrogen, $R^2$ is methyl.

2. A compound according to claim 1 wherein the compound is in a Z- and/or in an E-form.

3. A compound according to claim 1 wherein the compound is E-3-Methylcyclotetradec-5-en-1-one.

4. A compound according to claim 1 wherein the compound is Z-3-Methylcyclotetradec-5-en-1-one.

5. A compound according to claim 1 wherein the compound is (R)-E-3-Methylcyclotetradec-5-en-1-one.

6. A compound according to claim 1 wherein the compound is (S)-E-3-Methylcyclotetradec-5-en-1-one.

7. A compound according to claim 1 wherein the compound is (R)-Z-3-Methylcyclotetradec-5-en-1-one.

8. A compound according to claim 1 wherein the compound is (S)-Z-3-Methylcyclotetradec-5-en-1-one.

9. A compound according to claim 1 wherein the compound is E-2-Methylcyclotetradec-5-en-1-one.

10. A compound according to claim 1 wherein the compound is Z-2-Methylcyclotetradec-5-en-1-one.

11. A compound according to claim 1 selected from the group consisting of E-3-Methylcyclotetradec-5-en-1-one, Z-3-Methylcyclotetradec-5-en-1-one, (R)-E-3-Methylcyclotetradec-5-en-1-one, (S)-E-3-Methylcyclotetradec-5-en-1-one, (R)-Z-3-Methylcyclotetradec-5-en-1-one, (S)-Z-3-Methylcyclotetradec-5-en-1-one, E-2-Methylcyclotetradec-5-en-1-one, Z-2-Methylcyclotetradec-5-en-1-one, and mixtures thereof.

12. A scent composition comprising at least one compound according to claim 1.

13. A scent composition according to claim 12 wherein the compound is selected from the group consisting of E-3-Methylcyclotetradec-5-en-1-one, Z-3-Methylcyclotetradec-5-en-1-one, (R)-E-3-Methylcyclotetradec-5-en-1-one, (S)-E-3-Methylcyclotetradec-5-en-1-one, (R)-Z-3-Methylcyclotetradec-5-en-1-one, (S)-Z-3-Methylcyclotetradec-5-en-1-one, E-2-Methylcyclotetradec-5-en-1-one, Z-2-Methylcyclotetradec-5-en-1-one, and mixtures thereof.

14. A scent composition according to claim 12 wherein the composition is a perfume.

15. A process for preparing an organoleptic composition comprising: combining a compound according to claim 1 with a perfume or a consumer product.

16. A process according to claim 15 wherein the consumer product is selected from the group consisting of eaux de cologne, eaux de toilette, extraits, lotions, creams, shampoos, soaps, ointments, powders, deodorants, fabric softeners, and detergents.

* * * * *